(12) United States Patent
Yang (10) Patent No.: US 7,180,309 B1
(45) Date of Patent: Feb. 20, 2007

(54) ELECTRONIC SYSTEM FOR MULTIELECTRODE SENSORS AND ELECTROCHEMICAL DEVICES

(75) Inventor: Xiaodong Sun Yang, San Antonio, TX (US)

(73) Assignee: Corr Instruments, LLC., San Antonio, TX (US)

( * ) Notice: Subject to any disclaimer, the term of this patent is extended or adjusted under 35 U.S.C. 154(b) by 0 days.

(21) Appl. No.: 11/133,794

(22) Filed: May 21, 2005

Related U.S. Application Data (60) Provisional application No. 60/574,537, filed on May 26, 2004.

(51) Int. Cl.
*G01R 27/08* (2006.01)
(52) U.S. Cl. .................................. 324/700; 324/115
(58) Field of Classification Search ............... 324/700, 324/115
See application file for complete search history.

(56) References Cited

U.S. PATENT DOCUMENTS

| | | | | |
|---|---|---|---|---|
| 2,947,679 | A * | 8/1960 | Schaschl et al. ............ | 204/404 |
| 3,259,461 | A * | 7/1966 | Griffin, Jr. et al. ............ | 436/6 |
| 5,015,355 | A | 5/1991 | Schiessl | |
| 6,132,593 | A | 10/2000 | Tan | |
| 6,683,463 | B2 | 1/2004 | Yang | |
| 6,690,182 | B2 * | 2/2004 | Kelly et al. ................. | 324/700 |

OTHER PUBLICATIONS

U. Steismo, T. Rogne and J. M. Drugli, "Aspect of Testing and Selecting Stainless Steels for Sea Water Applications," CORROSION/94, Paper No. 492, Houston, TX: NACE International, 1994.

Y.J. Tan, "A New Crevice Corrosion Testing Method and its Use in the Investigation of Oil Stain," CORROSION, vol. 50, No. 4, pp. 266-269, 1994.

Z. Fei, R.G. Kelly and J.L. Hudson, "Spatiotemporal Patterns on Electrode Arrays," Journal of Phys. Chem., vol. 100, No. 49, pp. 18986-18991, 1996.

Y.J. Tan, "Monitoring Localized Corrosion Processes and Estimating Localized Corrosion Rates Using a Wire-beam Electrode," CORROSION, vol. 54, No. 5, pp. 403-413, 1998.

L. Yang et al., "An in-situ Galvanically Coupled Multielectrode Array Sensor for Localized Corrosion," CORROSION, vol. 58, No. 12, pp. 1004-1014, 2002.

L. Yang and N. Sridhar, "Coupled Multielectrode Online Corrosion Sensor," Materials Performance, vol. 42, No. 9, pp. 48-52, 2003.

H. Eren, et al., "An Auto-Switch for Multisampling of a Wire Beam Electrode Corrosion Monitoring System," IEEE Transactions on Instrumentation and Measurement, vol. 47, No. 5, pp. 1096-1101,1998.

* cited by examiner

*Primary Examiner*—Walter Benson (57) ABSTRACT

A basic electronic unit, an integrated electronic system, and the associated software program for coupled multielectrode electrochemical devices or sensors. The basic electronic unit uses different values of resistors for coupling the multiple electrodes in an electrochemical device or a sensor, so that the effective value of the coupling resistance can be dynamically changed according to the magnitude of the measured coupling current during the measurement. This feature allows the electronic unit to measure a wide range of coupling currents without compromising the principle that the coupled multielectrode electrochemical device simulates the one-piece metal behavior. The integrated electronic system uses several basic electronic units, so that it can simultaneously measure several independent multielectrode electrochemical devices or sensors that have a small number of electrodes, or measure one or more multielectrode devices or sensors that have a large number of electrodes. The software gives users the ability to change the data acquisition parameters dynamically during the measurements.

4 Claims, 11 Drawing Sheets

ELECTRONIC SYSTEM FOR MULTIELECTRODE SENSORS AND ELECTROCHEMICAL DEVICES

CROSS REFERENCE TO RELATED APPLICATIONS

This application claims the benefit of provisional patent application Ser. No. 60/574,537, filed 2004 May 26 by the present inventor.

BACKGROUND

1. Field of Invention

This invention relates to an electronic system and software for multielectrode sensors and other electrochemical devices.

2. Background

Coupled multielectrode array sensors (see U.S. Pat. No. 6,683,463 and U.S. Pat. No. 6,132,593) have been used for corrosion monitoring and electrochemical studies for some time now [L. Yang and N. Sridhar, "Coupled Multielectrode Online Corrosion Sensor," *Materials Performance*, 2003, September issue, page 48]. U.S. Pat. No. 6,683,463 to Yang and Sridhar (2004) disclosed a coupled multielectrode sensor system, in which each electrode is connected to a common joint through a resistor with substantially the same value as the resistors connected to other electrodes, and a multichannel high-precision voltmeter is used to scan the potential drop across each resistor to obtain the current flowing though the resistor. In a localized corrosion environment, some electrodes act as anodes and others act as cathodes; some of the anodes corrode more and produce high currents, and some of the anodes corrode less and produce low currents. The use of a single-valued resistor for all of the electrodes makes some electrodes at too high or too low potentials, which may compromise the simulation of a one-piece metal by the multiple electrodes. This is because the coupled multielectrode sensor concept requires that all of the electrodes of the multielectrode sensor operate at the same potential, just as the different sections of a one-piece metal are at the same potential. To date, there has been no software available that allows the flexible configuration of the multiple electrodes during measurements. This invention is related to a highly functional commercial instrument and a user-friendly and flexible software program for monitoring corrosion or studying electrochemical processes using the concept of multielectrode corrosion sensors or electrochemical devices.

REFERENCE NUMBERS OF DRAWINGS 5 basic electronic unit
6 voltage-measuring unit
10 electrode wires from a basic electronic unit for connection to the first through the last electrodes of a multielectrode device or a group of electrodes of a multielectrode device
12 coupling joint of a basic electronic unit
14 additional electrode
20 group of auto switches that are connected to each electrode in parallel (called K switches)
22 K switches (filled symbols indicate closed and open symbols indicate open state)
30 group of auto switches connecting each electrode to the voltmeter (called K" switches)
32 K" switches (filled symbols indicate closed state and open symbols indicate open state)
40 auto switch connecting the coupling joint to the voltmeter (called K' switch; filled symbols indicate closed state and open symbols indicate open state)
50 group of resistors that are between each electrode and the coupling joint (R group resistors)
51 R resistor #1 ($R_1$) with the lowest resistance value
52 R resistor #2 ($R_2$) with a higher resistance value
52 R resistor #j ($R_j$) with the highest resistance value
60 group of resistors in voltage-measuring unit that are in parallel with the R group resistors (called R' group resistors)
61 R' resistor #1 ($R'_1$) with the lowest resistance value
62 R' resistor #2 ($R'_2$) with a higher resistance value
62 R' resistor #j ($R'_j$) with the highest resistance value
70 group of auto switches that close or open the R'resistors (called K"" switches)
72 K"" switches (filled symbols indicate closed state, and open symbols indicate open state)
80 auto switches that connect between the coupling joints of any two or more basic electronic units (called K''' switches)
90 instrument panel
91 electrical connector for basic electronic unit (designated as Bank A, B, C, . . . for $1^{st}$, $2^{nd}$, $3^{rd}$, . . . basic electronic units)

92 electrical connector for two or more basic electronic unit (with more pins)

93 electrical connector for more basic electronic units (with even more pins)

94 numerical number showing the number of pins used on connector or available for measurement 96 connector connected to the coupling joint of a basic electronic unit (designated as A, B, C, . . . . for $1^{st}$, $2^{nd}$, $3^{rd}$, . . . basic electronic units)

102 cable that connects a group of wires from each basic electronic unit to the different types of electrical connectors

DETAILED DESCRIPTIONS AND OPERATIONS

Figure 1:
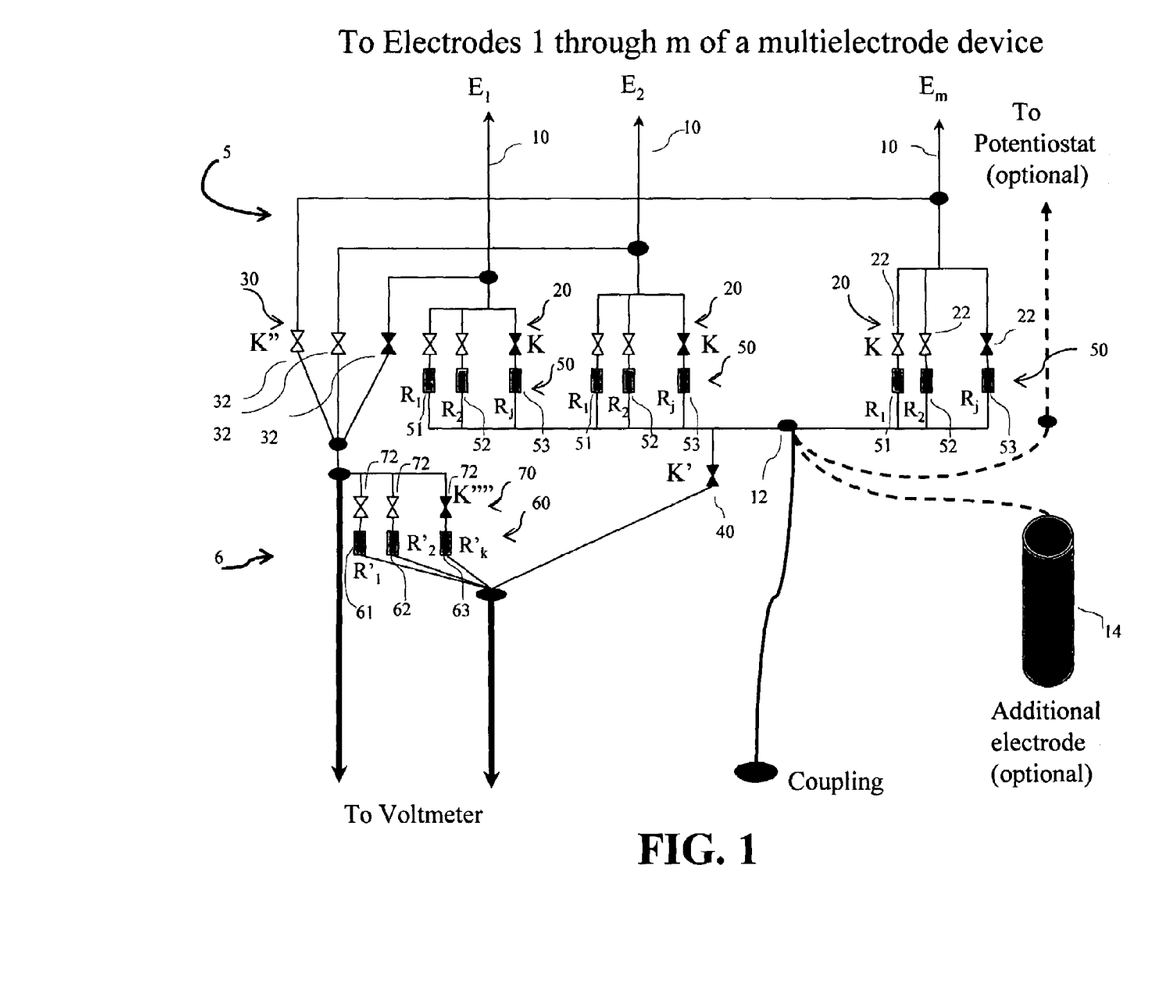
FIG. 1 is a schematic diagram of a basic electronic unit that uses a voltmeter to measure the coupling current from each electrode.
Figure 2:
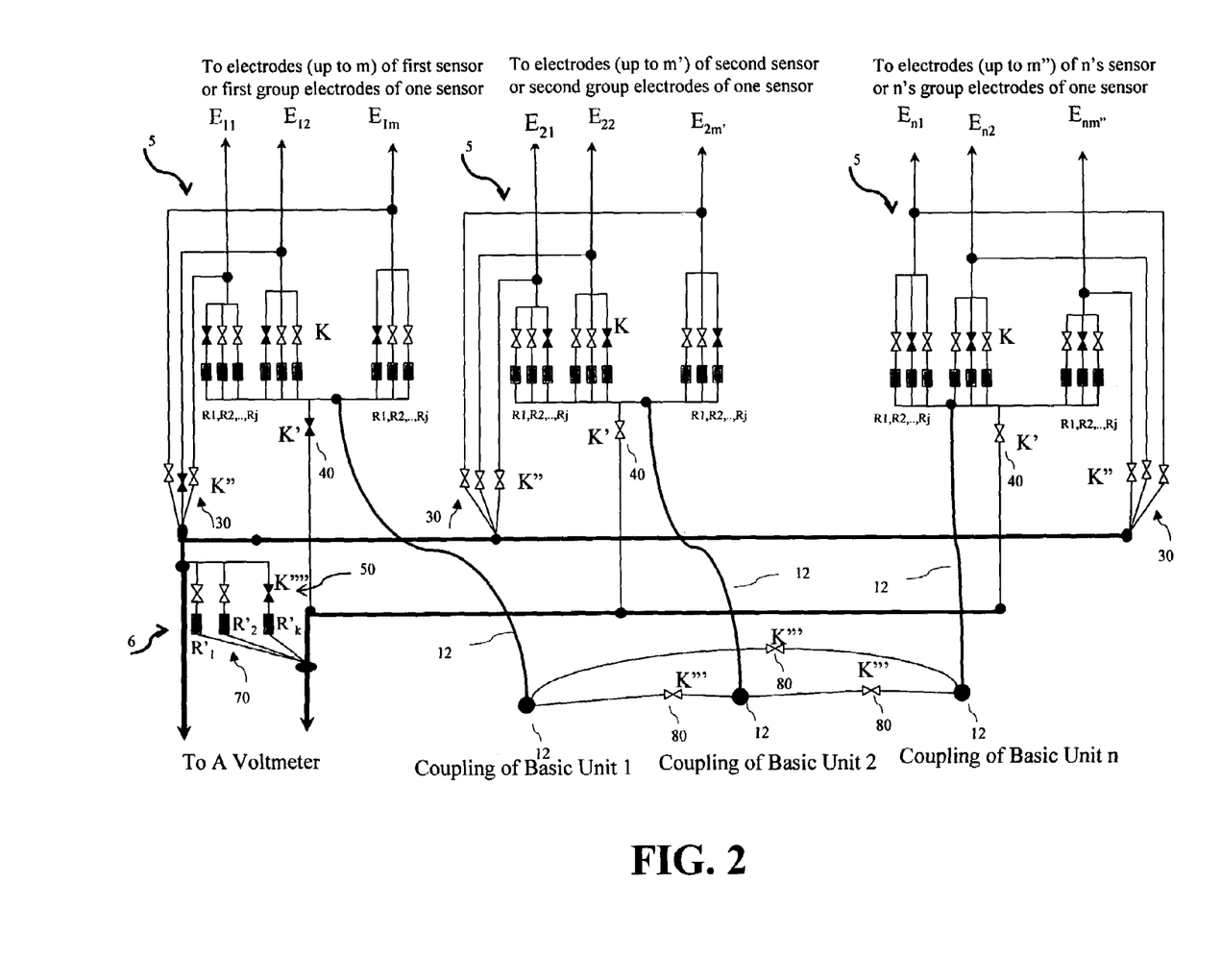
FIG. 2 is a schematic diagram of an integrated electronic system using a voltmeter to measure the coupling currents from the electrodes which are connected to a group of basic electronic units.
Figure 3:
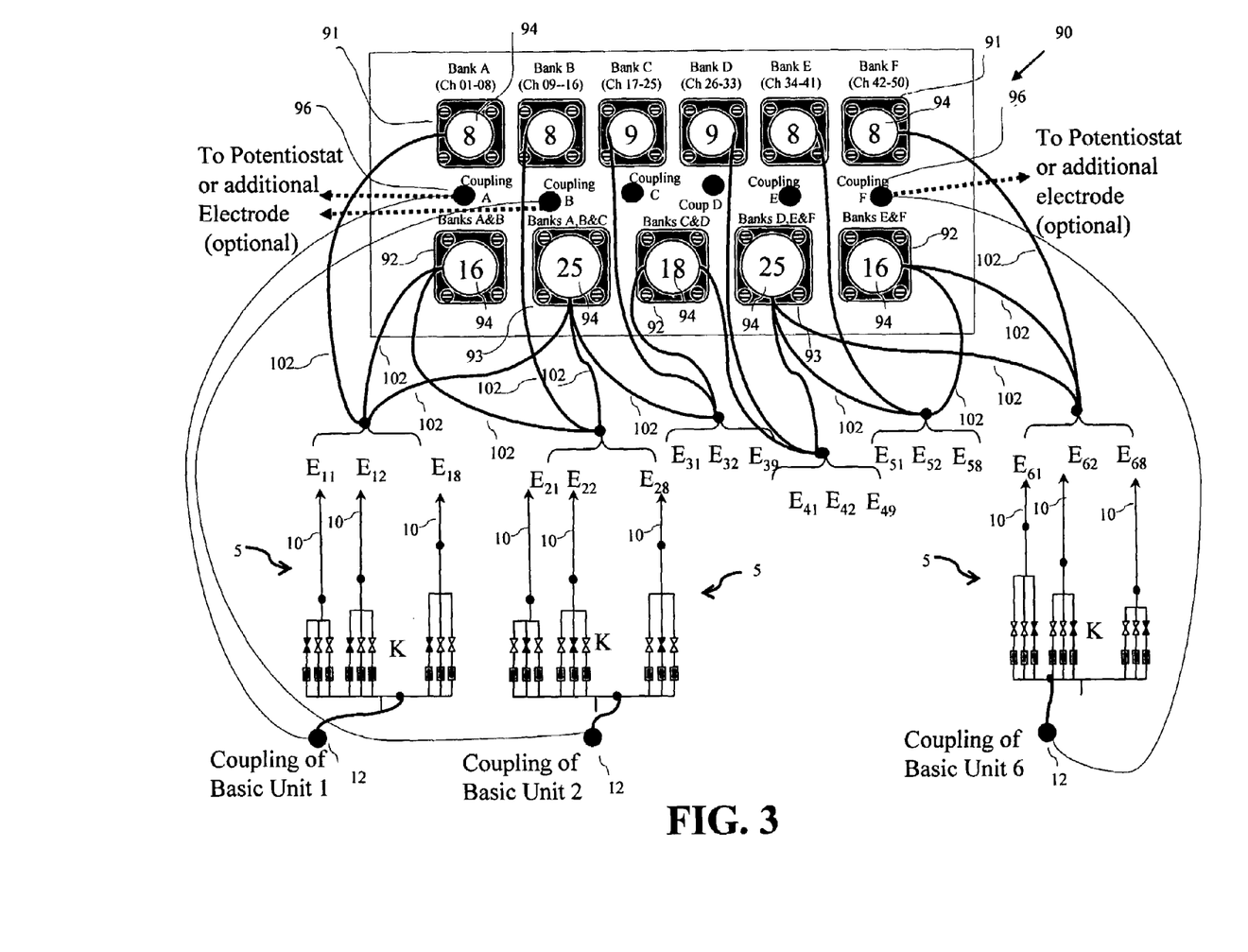
FIG. 3 is an example of the connections between different banks of multiple-pin connectors on an instrument panel and the electrode wires on the different basic electronic unit of an integrated electronic system.

FIGS. 1, 2 and 3—Electronic Hardware

FIG. 1 shows a schematic diagram of a basic electronic circuit 5 for measuring the coupling current from each electrode, by using a voltage-measuring unit 6 that has a voltmeter to measure the potential drop across the R resistors 50 and R' resistors 60. There are j different values of R resistors, 51 ($R_1$), 52 ($R_2$), . . . , and 53 ($R_j$) ($R_1 > R_2 > \ldots > R_j$) connected in parallel between the coupling joint 12 and the electrode wires 10, for connection to each electrode. With this connection, a suitable value of the parallel resister can be automatically selected to couple the electrodes in a multielectrode device or sensor or in a group of electrodes in a multielectrode device or sensor to one common coupling joint 12. The effective value of the R resistors 50 is such that the voltage across the R resistors 50 that are connected to the electrode wire 10 that has the largest current is small enough for all the electrodes connected to the electrode wires 10 to simulate the electrochemical behavior of a one-piece metal (the different sections of a one piece-metal are essentially at the same potential); and yet the small voltages across the other R resistors 50, connected to the other electrodes, are high enough for them to be accurately measured. The R resistors 50 that are used in the coupling are also called as the coupling resistors. Because the current from each electrode changes with time, the decision regarding which value of R resistor to use for coupling will be determined by a computer or a microprocessor, based on the dynamically measured current from each electrode. The selection of the proper R resistor is achieved by a computer or microprocessor, using the K switches 20 and 22 as shown in FIG. 1.

The K'' switches 30 and 32 are the scanning switches that control which of the electrode wires 10 is connected to the voltmeter during the measurement.

The K' switch 40 is used for isolation of the coupling joint 12 from the voltmeter, when no measurement is taken. The K'''' switches 70 and 72 may be used by a processor to control which of the R' resistors 60–61($R'_1$), 62 ($R'_2$), . . . , 63 ($R'_k$) ($R'_1 > R'_2 > \ldots > R'_k$, $k \geq 1$) to use to make the best measurement. The R' resistors 70 are also called the measuring resistors that can further adjust the potential drop between the electrode wires 10 and the coupling joint 12 so that the electronic unit is suitable for a large range of current. The R' resistors 70 are used to increase the current range the electronic unit can handle without the cost of adding more K switches 22 between each electrode wire 10 and the coupling 12.

The optional potentiostat or optional electrode 14 is used to alter the potential of the coupling joint 12. The optional electrode 14 may be a cathode that has a higher potential than the sensing electrodes or a large electrode. A cathode is usually used to raise the potential of the coupling joint 12 and a large electrode is usually used to stabilize the potential of the coupling joint 12. The optional electrode 14 may also be a system component such as the piping of a chemical process, the body of a large ship in seawater or the rebar in a concrete structure.

When a multielectrode device or sensor is used without being connected to the optional electrode 14, the sum or mean of the currents from all electrodes of a sensor should be zero.

FIG. 2 shows a schematic diagram of an integrated electronic system. In this system, a voltage-measuring unit that contains a voltmeter is used to measure the coupling currents from a group of basic electronic units 5. Each of the basic electronic units is used independently for all the electrodes in one multielectrode device or for a group of electrodes in a multielectrode device or sensor. The grouping of the electrodes allows users the flexibility of using one instrument (or integrated electronic system) either for several devices or sensors (up to n, as shown in FIG. 2), or for one device or sensor that has more electrodes (up to the sum of the number of electrodes in each group or each bank). Each basic electronic unit may be considered as an independent group of channels of the integrated electronic system. The reader will have a better understanding of this flexibility after reading the description section for software (below). When any of the two or more basic electronic units 5 are used for one sensor and their coupling joints 12 need to be coupled, the corresponding K''' switches 80 (which can also be manual switches and controlled manually) should be closed. Same value of resistors on the K switches 20 should be used for all the groups that are coupled together or used for one sensor. The other features described for FIG. 1, such as connections to a potentiostat or to an optional electrode 14, are not shown in FIG. 2, but can be easily understood by combining FIGS. 2 and 1.

FIG. 3 shows an example of the connections between the electrode wires 10 of a group of the basic electronic unit 5 (FIG. 2) and the electrical multi-pin connectors 91, 92, 93 on the instrument panel 90 through independent cables 102. The electrical connectors 91 for basic electronic units are designated as Banks A, B, C, . . . and F connectors, and they are connected to the $1^{st}$, $2^{nd}$, $3^{rd}$, . . . and $6^{th}$ basic electronic units, respectively. The electrical connectors 92 for two combined basic electronic units are designated as Banks A&B, C&D, and E&F connectors, and they are connected to the $1^{st}$ and $2^{nd}$, $3^{rd}$ and $4^{th}$, and $5^{th}$ and $6^{th}$ basic electronic units, respectively. The electrical connector 93 for three combined basic electronic units are designated as Banks A, B&C, and Banks D, E&F connectors and they are connected to the first three ($1^{st}$, $2^{nd}$, and $3^{rd}$) and the last three ($4^{th}$, $5^{th}$ and $6^{th}$) basic electronic units, respectively. Although not shown in FIG. 3, there may be other connectors in the panel. For example, a connector with an even larger number of pins may be used to connect all of the six combined basic electronic units.

Therefore, a user can use this instrument for: six sensors on electrical connectors 91, each having up to 8 or 9 electrodes, as indicated by the numerical number 94 in FIG. 3; three sensors on electrical connectors 92, each having up to 16 or 18 electrodes, as indicated by the numerical number 94 in FIG. 3, or two sensors on electrical connectors 93, each having up to 25 electrodes. A 50-pin electrical connector may also be added to the panel and connected to all of the six basic electronic units and used for a sensor having up to 50 electrodes. The user may also have other options. For example, he or she can use one 25-electrode sensor (with Bank A, B&C connector) and two 8-electrode sensors (with Banks E and F connectors) and one 9-pin electrode sensor (with Bank D connector).

When a connector is connected to more than one basic electronic units, the coupling joints of the corresponding basic units are usually connected by switching on the corresponding K''' switches (see FIG. 2). For example, if Banks A, B&C connector is connected to a sensor, the coupling joints of the $1^{st}$, $2^{nd}$, and $3^{rd}$ basic electronic units should be connected together. However, the user has the option of not switching on the corresponding K''' switches when using a connector connected to more than one basic electronic units for one sensor. For example, if a sensor with 25 electrodes is connected to Banks A, B&C connector, the user may choose not to connect the coupling joints of the 1st, $2^{nd}$, and $3^{rd}$ basic units. In this case, the user divides the electrodes in the sensor into three groups and the one 25-electrode sensor works as three sensors (two are 8-electrode sensors and one is a 9-electrode sensor). By properly specifying the options through use of the software (see the Software section), the user may have three processed sensor signals, such as: three corrosion rates, three corrosion potentials and three penetrations. By doing so, the user may check the reproducibility of three sub-sensors on a large sensor. However, it should be cautioned that the signals from an 8-electrode sensor may not be as reliable as the signals from a 25-electrode sensor according to the statistic principles.

FIGS. 4 Through 11—Instrument Software

Figure 4:
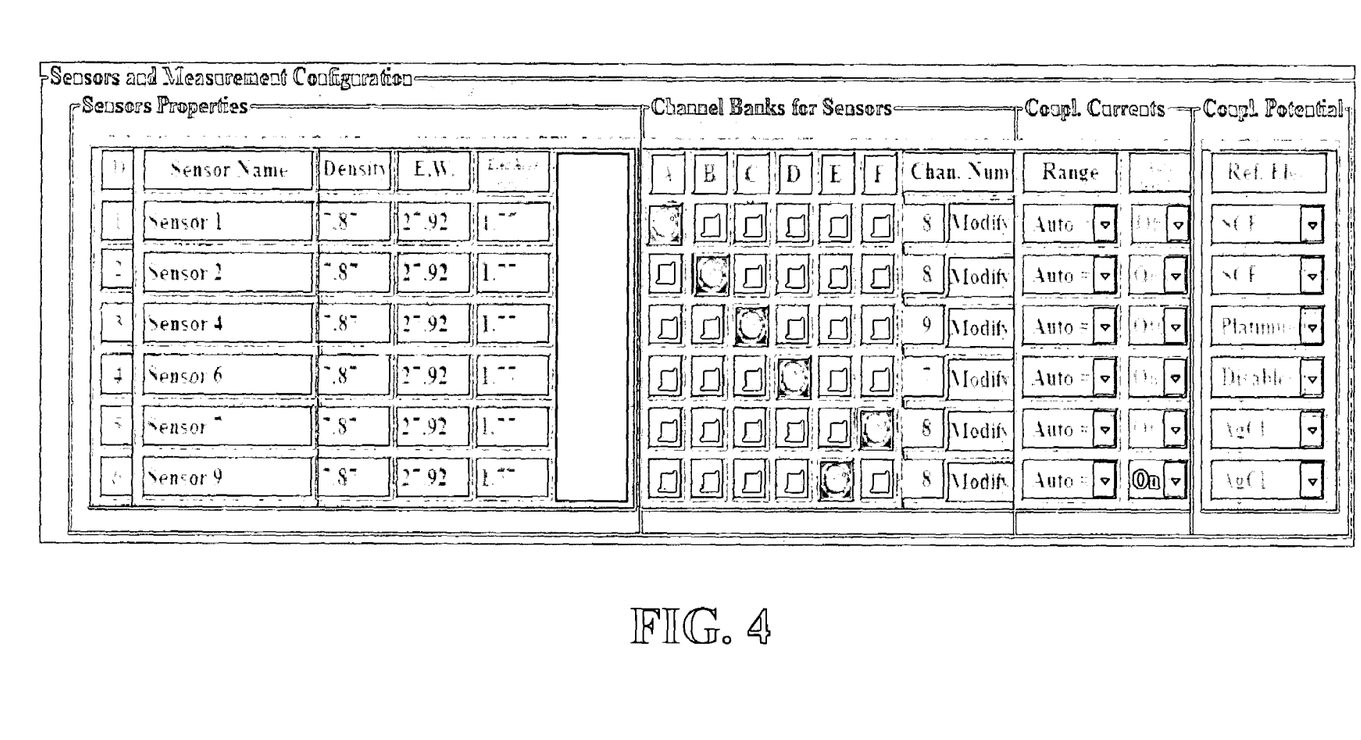
FIG. 4 shows one of the software interfaces for setting up the connections between the sensors and the connector banks on the instrument panel.

FIG. 4 shows one of the software interfaces for setting up the connections between the multielectrode devices or sensors and the connector banks 91, 92, and 93 on the instrument panel 90. In FIG. 4, Sensors 1, 2, 4, and 6 use connector Banks A through D, respectively; Sensor 7 uses Bank F; and Sensor 9 uses Bank E. The Chan. Num. (channel number, or called the active pin number or electrode number) is the number of active channels or active pins on a connector (Note: the numerical number 94 in FIG. 3 is the number of pins available for measurement on a connector). The Chan. Num. can be modified, by clicking the corresponding Modify button (see below for details). The Density, E.W. (Equivalent Weight) and Elec. Area (electrode surface area in $mm^2$) parameters are required by the software, to calculate the corrosion rate, in terms of depth per unit time (or growth rate, if the instrument is used to study the electroplating processes) and corrosion penetration, in terms of depth. The Auto Mean Zero option is used to tell the software whether or not to automatically correct the bias currents according to the multielectrode sensor principles. As discussed earlier (see the discussion section for FIG. 1), when the coupling joint is not connected to a separate electrode, the sum of the cathodic and anodic currents from a coupled multielectrode device or sensor should be zero and the mean value should also be zero. Any deviation from zero is caused by an error or bias current and should be corrected. The Reference Electrode option is for specifying what reference electrode is used to measure the potential of a multielectrode device or sensor (the potential at the coupling joint 12) using a separate voltmeter or using the same voltage measuring unit 6 with an added separate switch equivalent to the K" switch 30 as shown in FIG. 1.

The Range option is to specify what range of the instrument to use; usually the Auto range is used. The number of ranges on the basic electronic unit equals the product of j and k (or j times k), as shown in FIG. 1.

Figure 5:
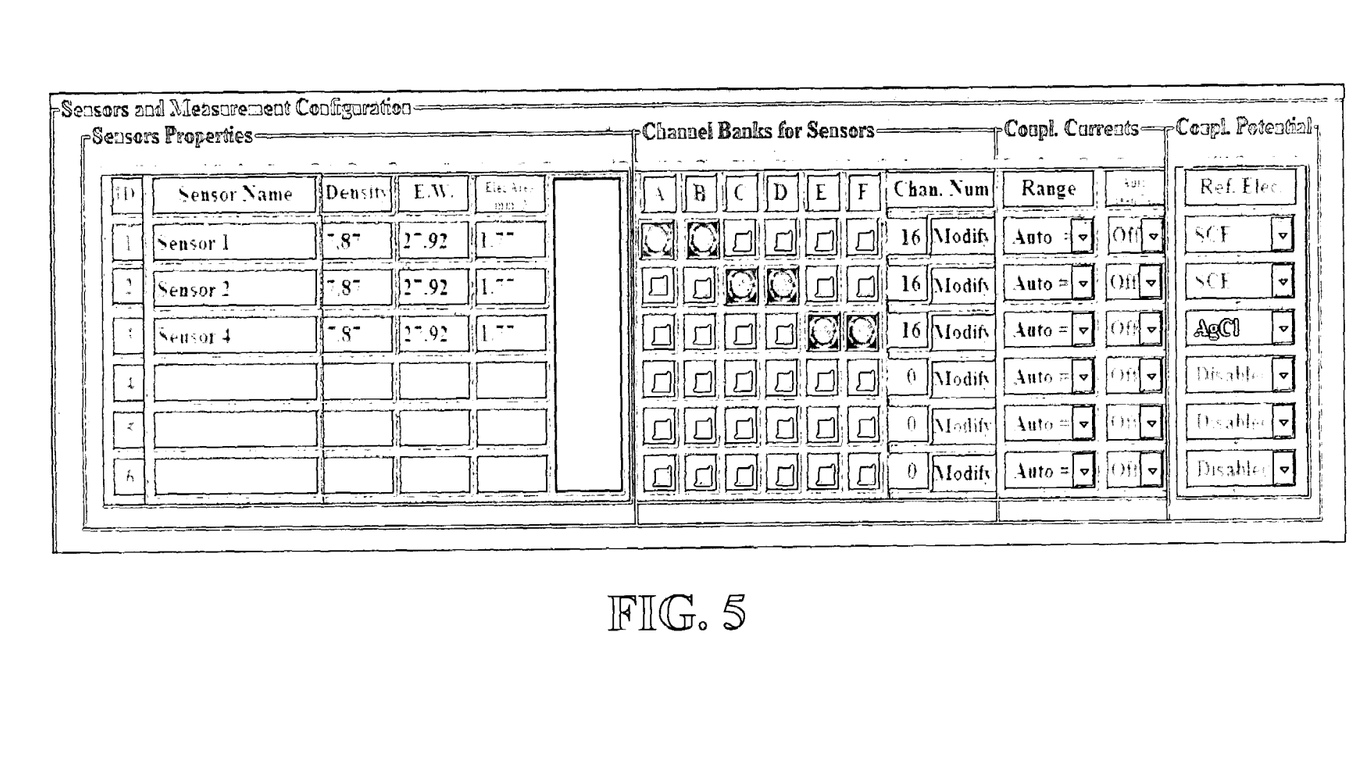
FIG. 5 shows a variation of the specifications for the software interface as shown in FIG. 4.

FIG. 5 shows a variation of the specifications for the software interface, as shown in FIG. 4. Here, Sensor 1, which has 16 active electrodes, uses Banks A and B; Sensor 2, which has 16 active electrodes, uses Banks C and D; and Sensor 4, which also has 16 active electrodes, uses Banks E and F.

In FIG. 5, a user can utilize any combination of the connectors 91, 92, and 93 for a given sensor. For example, the user can use Banks A, B, D, E and F for a sensor. If the sensor only needs a portion of the pins on some of the connectors, the user needs to go to FIG. 6 to deactivate those that are not required (see next paragraph).

Figure 6:
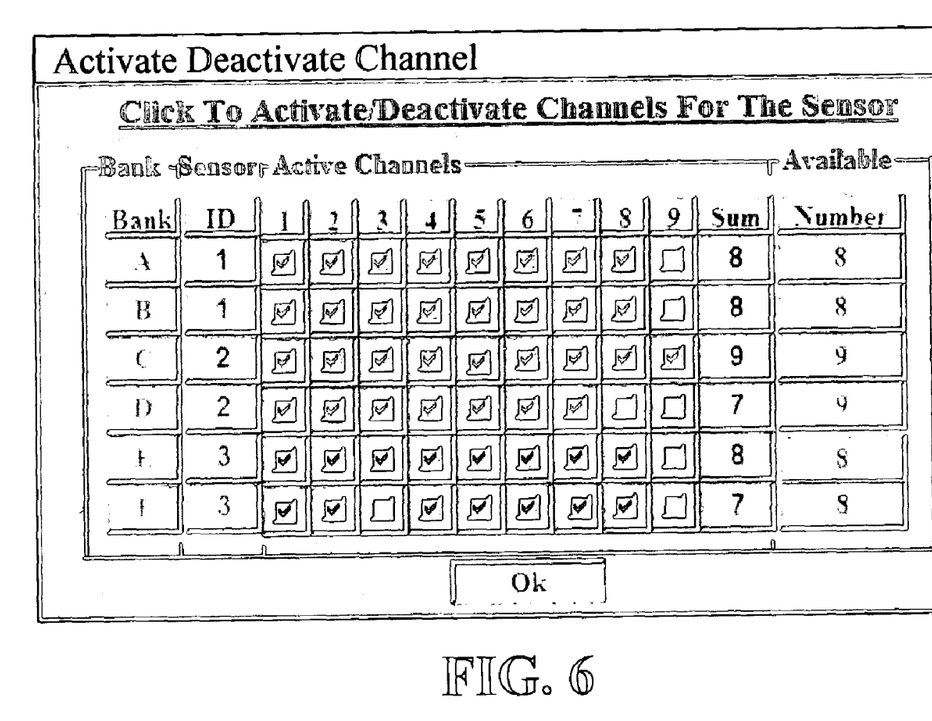
FIG. 6 shows the software interface for specifying which pin/channel (or electrode) is active or inactive for each bank of connectors.

FIG. 6 shows the software interface for specifying which pin/channel (or electrode wire 10) is active or inactive for each bank of connectors 91, 92, and 93. The user can click on a check box in FIG. 6 to activate or deactivate the corresponding pin/channel. The number in the Sum column is automatically calculated after the user activates or deactivates a pin/channel. The numbers in the Available Number column are the values of m, m', and m", as shown in FIG. 2, or the numerical number 94, as shown in FIG. 3, and they are fixed at the instrument design time. In FIG. 6, Pin 3, on Connector Bank F, and Pins 8 and 9, on Connector Bank D, are deactivated. All of these three pins are available on the instrument, by design.

Figure 7:
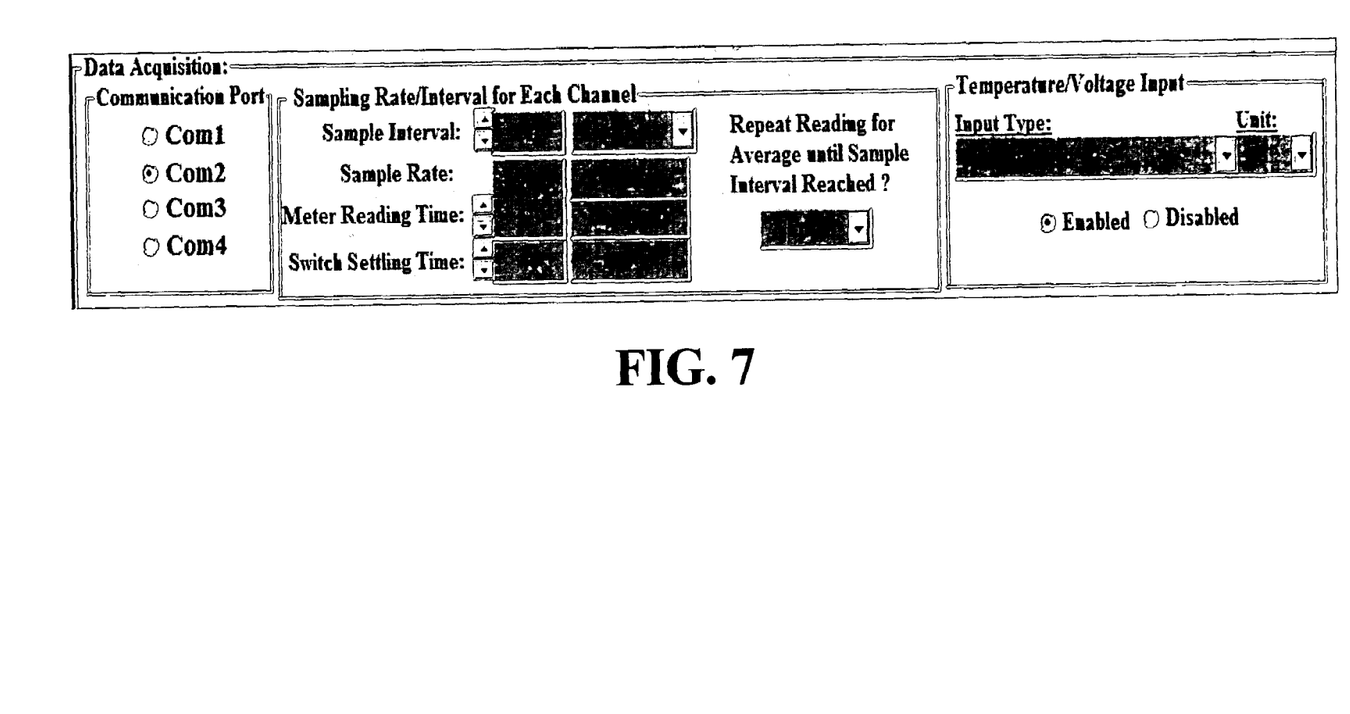
FIG. 7 shows the software interface for specifying the data files to save the collected and the processed data during the measurements.

FIG. 7 shows the software interface for specifying the data files to save the collected and the processed data during the measurements. Because of the large number of data available from multielectrode devices or sensors, the data are saved into five files according to their category or type. The first file contains the main corrosion data, such as the corrosion rate, the penetration depth (if the sensor electrode area and E.W. are given), the corrosion potential for each sensor, and the temperature. Corrosion current and corrosion cumulative charge will be saved, instead of the corrosion rate and penetration, if the electrode area and the E.W. are not given. The second file contains all corrosion-related data, such as corrosion current, corrosion current density, corrosion charge, corrosion charge density, corrosion rate, corrosion depth, corrosion potential, which electrode is corroding the most, and which electrode has corroded the most on each sensor at each time interval. The third file contains the currents from all electrodes, on every sensor. The user has the option to not save the corrosion potential to reduce the file size. The fourth file contains the statistics for the signals from all electrodes in each sensor. The statistic parameters include the mean, minimum, maximum and standard deviation of currents, and minimum and maximum charges for each sensor. The user also has the option to choose not to save the corrosion potential data for each sensor to reduce the file size. The fifth file contains all available data. The other options are self-explanatory. For each file, the user has the option of not using it to reduce the total memory size. This kind of file saving method gives the user a great flexibility in using the instrument. For example, a plant operator is usually concerned with only the corrosion rate. Therefore, he or she can choose to disable all the other files. On the other hand, a researcher in an electrochemical laboratory may want to gather and keep all the information from a multielectrode device or sensor. In this case, he or she may want to enable only the fifth file or to enable all the first four files.

Figure 8:
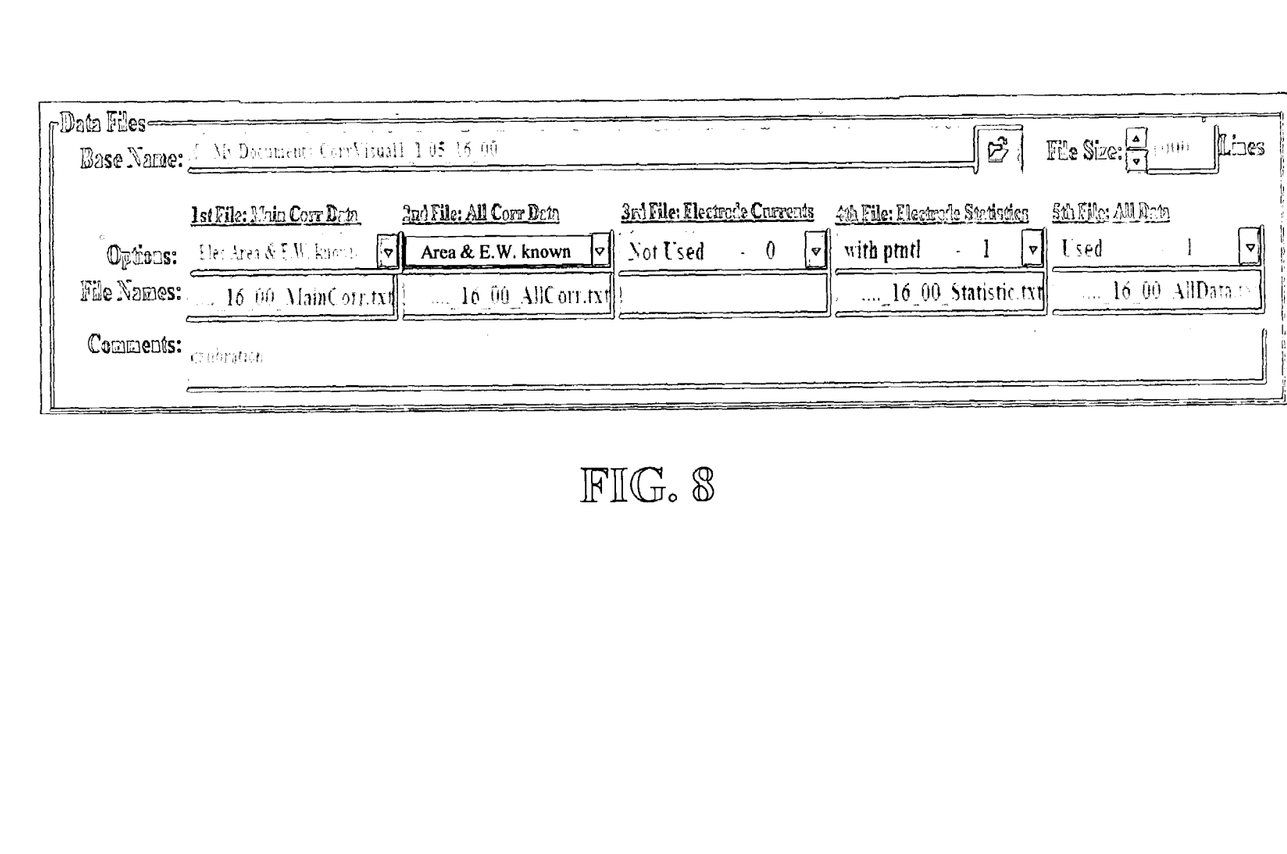
FIG. 8 shows the software interface for specifying the Meter Reading Time, Switch Settling Time, and whether or not a user wants to repeat readings for averaging during a given time interval.

FIG. 8 shows the software interface for specifying Meter Reading Time (for the voltmeter plus the electronic unit 5 or integrated electronic system), Switch Settling Time, and whether a user wants to Repeat Readings for Averaging during a given time interval. The Sample Interval is the time interval a user specifies to sample one data point for every active electrode connected to the instrument. The Meter Reading Time is the time it takes for the meter to read once from all the electrodes. The Switch Settling Time is how long a user wants the meter to wait after the K" switch (see FIG. 1) is switched on before taking the reading for an electrode. The user can adjust this time to minimize the effects of the spikes that may be produced by the switching. If the settling time is long enough, the meter will start to take readings after the spike has disappeared. The Meter Reading Time includes the Switch Settling Time and the integration time for taking the reading for every channel (or electrode). If the Meter Reading Time is set long enough, the meter will take the maximum possible integration time to get a stable and accurate reading before going to the next channel (or electrode). In many cases, the Meter Reading Time is much shorter then the Sample Interval. Therefore, the meter is able to repeat the reading cycle many times and then get an averaged result for each electrode at the end of the Sample Interval to filter out possible noise effect. Users can do so by selecting the option of "Repeat Reading for Averaging until the Sample Interval Reached." This filtering is important for the measurement of extremely low corrosion rates (down to 10 nm/year) or low currents (down to 10 pA). The other features in this interface are self-explanatory.

Figure 9:
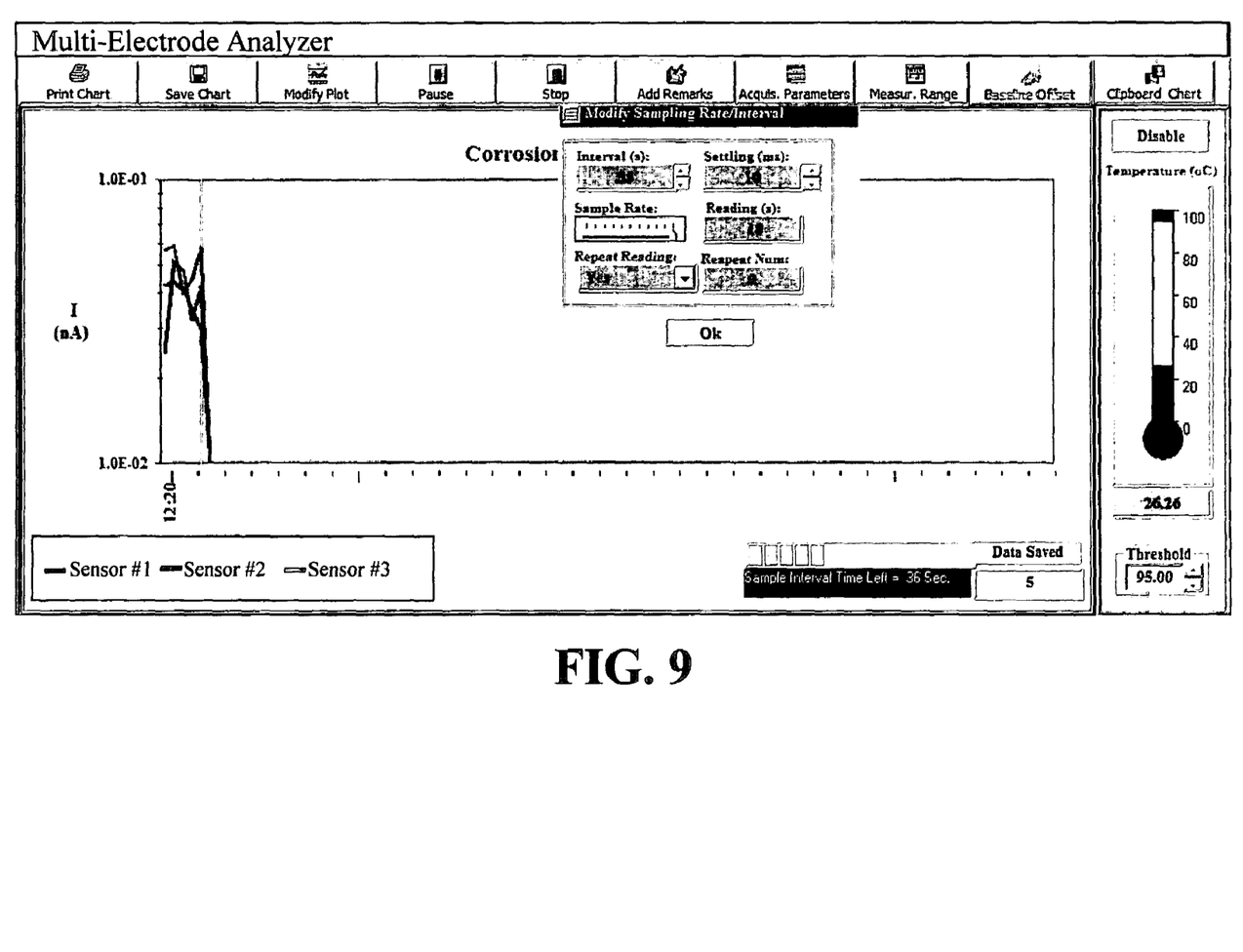
FIG. 9 shows the software interface that appears during measurement or monitoring.

FIG. 9 shows the software interface that appears during measurement or monitoring. This interface not only dynamically displays the measured data, but also allows a user to change the data acquisition parameters such as the Sample Interval, Settling Time, and Sample Rate during the measurement. The interface also allows a user to pause the measurement in order to alter the experiment (i.e., taking a sensor out of a monitoring location to inspect the degree of corrosion taking place on the electrode surfaces). The measurement range for each sensor can also be changed from this user interface.

The Add Remarks option is like an electronic notebook. This button allows a user to add remarks; the software will automatically record them and the time they are made into the Remarks column of every data file and into a separate Remarks file. The software also automatically records all the changes the user made to the program, such as Measure Range changes (including the old range and the new range) or Acquis. Parameters changes (including the parameter name, and the old value and the new value) to the Remark column of every data file and to the separate Remarks file.

Figure 10:
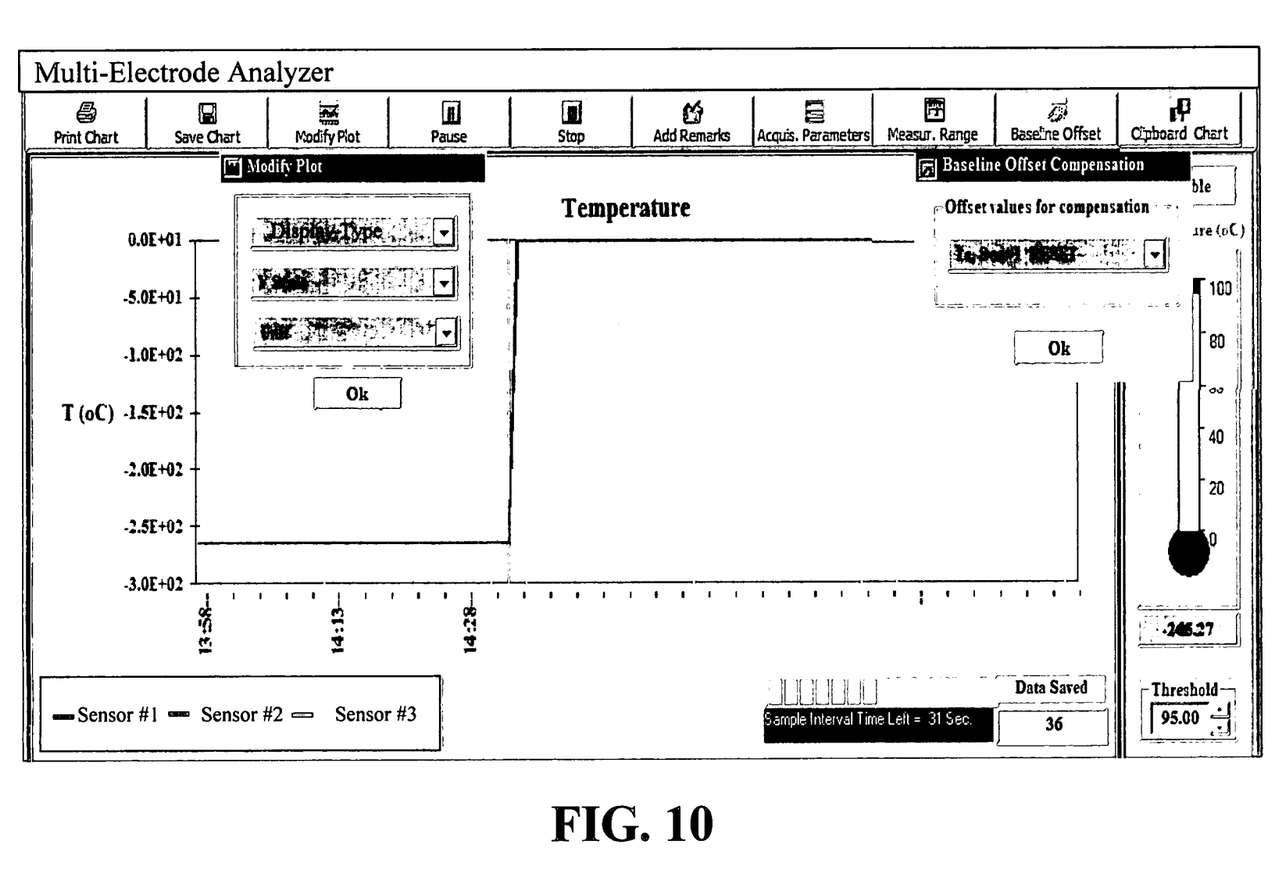
FIG. 10 shows the features of Modify Plot and Baseline Offset corrections on the software measurement interface.

FIG. 10 shows the features of Modify Plot and Baseline Offset corrections on the software measurement interface. The Baseline Offset button allows a user to reset, disable/enable or obtain new baseline offset values. The baseline offset for each channel is the current measured when that channel is connected to a zero current source. Because the instrument measures currents by measuring the voltages across the resistors (see FIGS. 1 and 2), such low levels of baseline offset are usually caused by the thermoelectric effect from the electrical contacts. The baseline offset values for each channel (or electrode) can be measured while the sensor is placed in dry air, where it should have zero corrosion currents and be stored in the memory of a controller or a computer. These offset values, if the option on the interface is enabled, are used by the software to automatically correct the small baseline offset errors from each electrode for better accuracy. The software is also able to display different types of dynamic plots (including the corrosion rate, corrosion penetration depth, corrosion current, corrosion current density, corrosion potential, and temperature).

Figure 11:
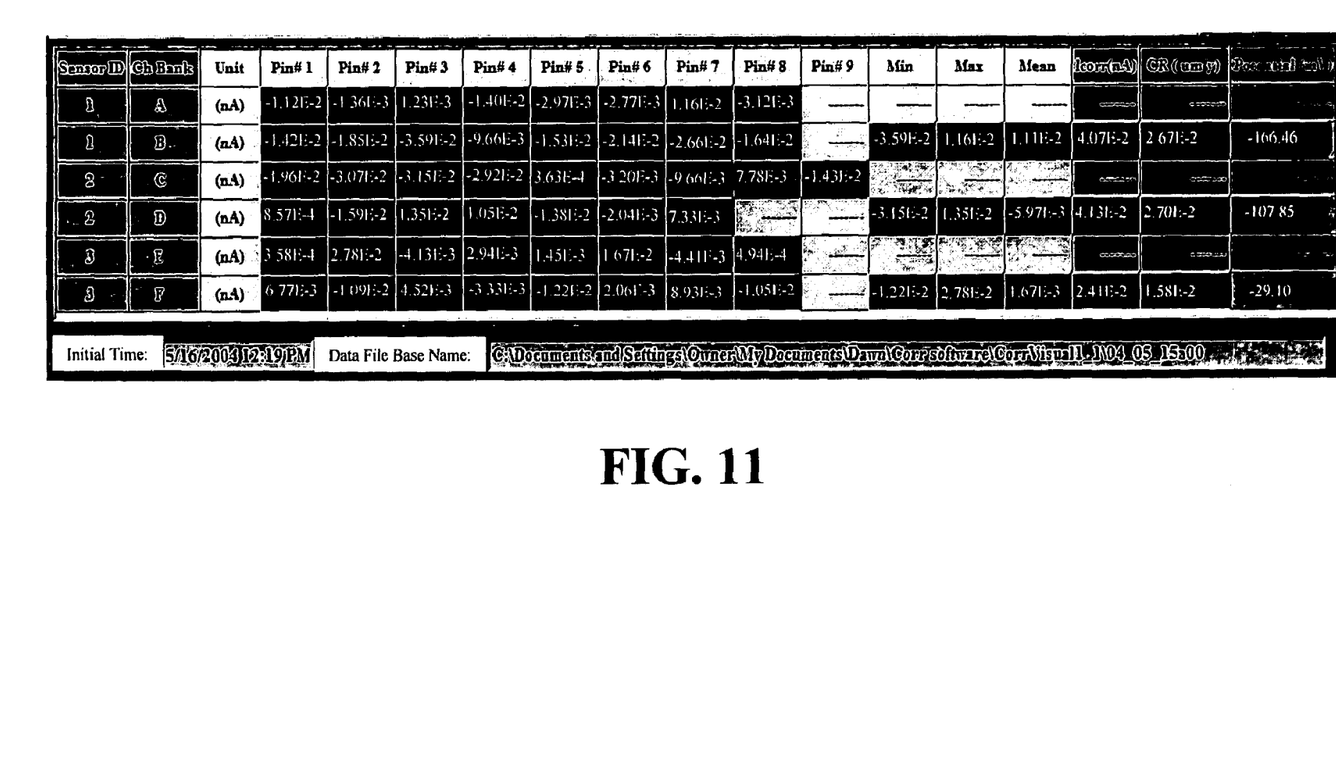
FIG. 11 shows that the software measurement interface dynamically displays the numerical values for the currents from all electrodes and the statistic parameters (such as minimum, maximum and mean, and the corrosion rate and corrosion potential for each sensor).

FIG. 11 shows that the software measurement interface dynamically displays the numerical values for the currents from all electrodes and the statistic parameters, such as minimum, maximum and mean, and the corrosion rate and corrosion potential for each sensor.

Advantages

From the description above, a number of advantages of the invention become evident:

(a) Using a group of resistors (R resistors) and the associated auto switches (K switches) for the coupling of the electrodes in a multielectrode device or sensor, rather than a single resistor, enables the electronic system to be used in a wide range of coupling currents without causing a significant deviation from simulating the one-piece metal behavior.

(b) With the use of one or more R' resistors and the associated switches (K" switches) in the voltage measuring unit, users can extend the coupling current range without the need to add additional R resistors for each electrode. This eliminates the cost of the auto switches associated with each of the additional R resistors.

(c) Utilizing several basic electronic units in one larger electronic system enables users to use the electronic system to simultaneously measure several independent multielectrode electrochemical devices or sensors that have a small number of electrodes, or to measure one or more multielectrode devices or sensors that have a large number of electrodes.

(d) With a small-sized multiple-pin connector wired to each basic electronic unit and one or more large-sized multiple-pin connectors that are each wired to two or more of the basic electronic units, the instruments can be conveniently used either for several electrochemical devices or sensors with smaller number of electrodes, or one or more electrochemical devices or sensors with a larger number of electrodes.

(e) With a software program that has the ability to allow users to enable or disenable some of the electrodes on a multielectrode devices or sensors, the instruments can be used to measure only a select number of the electrodes on a multielectrode device or sensor according to its location. This function is especially useful for researchers in a laboratory to study the spatial behavior of electrochemical processes.

(f) With the option to save data into several files, the software allows users to work more efficiently with greatly reduced number of data in selected files.

(g) The interface for a user to enter information and notes, which are saved into the separate Remarks file along with the time stamp, and saved into the Remarks column of the data files along with the data acquired during the same time interval, eliminated the need for the user to have a hardcopy of laboratory notebook.

(h) The ability to change the data acquisition parameters dynamically during the measurements eliminates the need for users to restart the measurement each time they want to change the parameters.

OTHER EMBODIMENTS

Although the description above contains many specificities, these details should not be construed as limiting the scope of the invention, but merely as providing illustrations of some of the presently preferred embodiments of this invention. Thus, the scope of the invention should be determined by the appended claims and their legal equivalents, rather than by the examples.

The invention claimed is:

1. A basic electronic unit for the measurement of the current from each electrode of a multielectrode electrochemical device or corrosion sensor, with a voltage measuring unit, comprising:
   (a) a plurality of electrode wires or channels for connection to the electrodes of a multielectrode device
   (b) a common coupling joint
   (c) a group of two or more resistors connected in parallel between each electrode wire and the common coupling joint as coupling resistors and
   (d) switching means for the resistors, which allow a controller to change the effective value of the group of parallel resistors so that the voltage across the group of the parallel resistors is low enough for the multielectrode device to simulate the electrochemical behavior of one-piece metal, and yet high enough to be reliably measured by said voltage measuring unit.

2. An electronic unit of claim 1 and a voltage measuring unit comprising:
   (a) one or more resistors connected in parallel between the two wires (high and low) for connection to a voltmeter
   (b) switching means for resister(s), which allows a controller to change the effective value of the resistance between the two wires so that the voltage across the group of the parallel coupling resistors is low enough for the multielectrode device to simulate the electrochemical behavior of one-piece metal, and yet high enough to be reliably measured by said voltage measuring unit in a large range of currents.

3. An integrated electronic system, comprising:
   (a) Two or more independent electronic units for the measurement of the current from each electrode of a multielectrode device, comprising:
       (1) a plurality of electrode wires or channels for connection to the electrodes of a multielectrode device
       (2) a common coupling joint
       (3) a group of two or more resistors connected in parallel between each electrode wire and the common coupling joint as coupling resistors, and
       (4) switching means for the resistors, which allow a controller to change the effective value of the group of parallel resistors so that the voltage across the group of the parallel resistors is low enough for the multielectrode device to simulate the electrochemical behavior of one-piece metal, and yet high enough to be reliably measured by a voltage measuring unit,
   (b) switches between the coupling joints of the independent electronic units,
   (c) voltage measuring unit, connected to the independent electronic units in such a way that gives a user the flexibility to use each of the independent electronic units for one multielectrode device with smaller number of electrodes, to use two or more of the basic electronic units for one multielectrode device with a larger number of electrodes, or to use all the independent electronic units for two or more independent multielectrode devices simultaneously.

4. An integrated electronic system of claim 3 and an instrument panel comprising:
   (a) a plurality of small-sized multiple-pin connectors, each being independently connected to the electrode wires on one of the basic electronic units and
   (b) one or more large-sized multiple-pin connectors, each being connected to the electrode wires on two or more of the basic electric units so that electrochemical devices or sensors with smaller number of electrodes can be conveniently connected to the small-sized connectors and the electrochemical devices or sensors with larger number of electrodes can be conveniently connected to the large-sized connectors that are connected to two or more of the basic electronic units.

* * * * *